US008093457B2

(12) United States Patent
Hehl et al.

(10) Patent No.: US 8,093,457 B2
(45) Date of Patent: Jan. 10, 2012

(54) STORAGE-INDUCED PROMOTER

(75) Inventors: Reinhard Hehl, Braunschweig (DE); Alexander Rotthues, Bad Soden am Taunus (DE); Dietmar Juergen Stahl, Einbeck (DE)

(73) Assignee: KWS SAAT AG, Einbeck (DE)

( * ) Notice: Subject to any disclaimer, the term of this patent is extended or adjusted under 35 U.S.C. 154(b) by 1232 days.

(21) Appl. No.: 11/720,252

(22) PCT Filed: Nov. 23, 2005

(86) PCT No.: PCT/DE2005/002093
§ 371 (c)(1),
(2), (4) Date: May 25, 2007

(87) PCT Pub. No.: WO2006/056176
PCT Pub. Date: Jun. 1, 2006

(65) Prior Publication Data
US 2011/0041212 A1 Feb. 17, 2011

(30) Foreign Application Priority Data
Nov. 26, 2004 (DE) .......................... 10 2004 057 291

(51) Int. Cl.
C12N 15/82 (2006.01)
A01H 5/00 (2006.01)
C07H 21/04 (2006.01)

(52) U.S. Cl. ........ 800/287; 800/279; 800/284; 800/289; 800/295; 800/298; 536/24.1; 435/320.1; 435/419; 435/468

(58) Field of Classification Search .......................... None
See application file for complete search history.

(56) References Cited

U.S. PATENT DOCUMENTS

| 6,084,089 | A | 7/2000 | Mine et al. |
| 6,531,649 | B1 | 3/2003 | Mannerloef et al. |
| 6,700,039 | B1 | 3/2004 | Jepson et al. |
| 7,563,944 | B2 | 7/2009 | Heim et al. |
| 2004/0049803 | A1 | 3/2004 | Kellogg et al. |
| 2004/0064853 | A1 | 4/2004 | Hehl et al. |

FOREIGN PATENT DOCUMENTS

| EP | 0812917 | | 12/1997 |
| EP | 0812917 | B1 | 12/1997 |
| WO | 0031251 | A1 | 6/2000 |
| WO | WO 00/21251 | * | 6/2000 |
| WO | WO 00/31251 | | 6/2000 |
| WO | 2004065537 | A2 | 8/2004 |

OTHER PUBLICATIONS

Satoh et al. *Beta vulgaris* subsp. vulgaris mitochondiral genomic DNA, complete sequence. (2004) GenBank Access BA000024; pp. 1-108.*
Trindale et al. Analysis of genes differentially expressed during potato tuber life cycle and isolation of the promoter regions. (20040 Plant Science; vol. 166; pp. 423-433.*

Clendennen et al. Differential gene expression in ripening banana fruit. (1997) Plant Phys.; vol. 115; pp. 463-469.*
Dopico et al. Cloning and characterization of avocado fruit mRNAs and their expression during ripening and low-temperature storage. (1993) PMB; vol. 21; pp. 437-449.*
Trindade, et al.; Analysis of genes differentially expressed during potato tuber life cycle and isolation of thie promoter regions; Plant Science 166(2004) 423-433.
Haslekas, et al.; The expression of a peroxiredoxin antioxidant gene, AtPer1, in *Arabidopsis thaliana* is seed-specific and related to dormancy; Plant Molecular Biology; 36: 833-845, 1998.
XP-002371885, Mar. 27, 2004; Trindade L.M., Visser R.J.R.; *Solanum tuberosum* L362 gene, complete sequence.
XP-002371884, Mar. 27, 2004; Trindade L.M., Horvath B.M., van Berloo R., Visser R.G. F.; *Solanum tuberosum* L363 gene, complete sequence.
Agrimonti et al. "In vitro and in silico analysis of two genes (A2-1 and G1-1) differentially regulated during dormancy and sprouting in potato tubers" Division of Genetics and Environmental Biotechn., Department of Environmental Sciences, University of Parma, Italy Potato Research 43 (2000), pp. 325-333.
Reilly et al. "Isolation and characterisation of a cassava catalase expressed during post-harvest physiological deterioration" Department of Biology and Biochemistry, University of Bath, UK, CIAT, A.A. 6713, Cali, Colombia Biochimica et Beiophysica Acta 1518 (2001) pp. 317-323.
Han et al. "Hydroxyproline-rich glycoproteins expressed during stress responses in cassava" Department of Biology and Biochemistry, University of Bath, UK, CIAT, A.A. 6713, Cali, Colombia Euphytica 120 (2001), pp. 59-70 Kluwer Academic Publishers. Printed in the Netherlands.
Rotthues et al. Post-harvest regulated gene expression and splicing efficiency in storage roots of sugar beet (*Beta vulgaris* L.) Planta (2008) 227, pp. 1321-1332 Springer-Verlag 2008, Germany.
Li Rugang et al. "Transgenic Potato Plants Expressing Osmotin Gene Inhibits Fungal Development in Inoculated Leaves" Chinese Journal of Biotechnology (1999), vol. 15, No. 2, pp. 71-75 Biotechnology Research Center, Chinse Academy of Agricultural Scienes, Beijing, China.
Mitsuhara et al. "Efficient Promoter Cassettes for Enhanced Expression of Foreign Genes in Dicotyledonous and Monocotyledonous Plants" Plant Cell Physiol 37(1) (1996), pp. 49-59 Japan.
Benfey et al. "Tissue-specific expression from CaMV 35S enhancer subdomains in early stages of plant development" The EMBO Journal vo. 9 No. 6 (1990), pp. 1677-1684 Laboratory of Plant Molecular Biology, Rockefeller University, NY, USA.
Zhijian Li et al. "Expression of a bifunctional green fluorescent protein (GFP) fusion marker under the control of three constitutive promoters and enhanced derivatives in transgenic grape (*Vitis vinifera*)" Plant Science 160 (2001), pp. 877-887 Mid-Florida Research and Education Center, Intistute of Food and Agricultural Scienes, University of Florida, USA.

(Continued)

*Primary Examiner* — Cathy Kingdon Worley
(74) *Attorney, Agent, or Firm* — Patent Central LLC; Stephan A. Pendorf

(57) ABSTRACT

The invention relates to a promoter with an organ-specific activity in plants. Said promoter is characterised in that it exhibits greater activity in the storage organs of plants than in other organs of said plants and that the promoter activity is modified after the harvest of the storage organs and is greater than prior to said harvest.

11 Claims, 7 Drawing Sheets

OTHER PUBLICATIONS

Kay et al. "Dublication of CaMV 35S Promoter Sequences Creates a Strong Enhancer for Plant Genes" Science, vol. 236 (1987), pp. 1299-1302 Department of Botany, University of British Colombia, Vancouver, Canada.

Schneider et al. "Expression Patterns and Promoter Activity of the Cold-Regulated Gene ci21A of Potato1" Plant Physiol. (1997) 113, pp. 335-345 Max-Planck Institute, Cologne, Germany.

Eguchi et al. "Non-contact measurements of storage organ growth in fruit and root crops" Environment Control in Biology 45 (4) (Dec. 2007), pp. 251-258, ISSN: 1880-554X Japan ISI Web of Knowledge.

Decision to refuse the European application No. 05 817 889.8 dated Oct. 2, 2008 No equivalent English document available.

Riov, J. "A Polygalacturonase from Citrus Leaf Explants" Department of Horticulture, The Hebrew University of Jerusalem, Rehovot, Israel Plant Physiol. (1974) 53, pp. 312-316.

Botella, Miguel A., et al. "Differential Expression of Soybean Cysteine Proteinase Inhibitor Genes during Development and in Response to Wounding and Methyl Jasmonate", Center for Plant Environmental Stress Physiology, Indiana, and Department of Biological Sciences, State University of New York at Binghamton, New York Plant Physiol. (1996) 112, pp. 1201-1210.

Hou, Wen-Chi, et al. "Chitinase activity of sweet potato (*Ipomoea batatas* [L.] Lam var.Tainong 57)" Institut of Botany, Academia Sinica, Nankang, Taiwan, Republic of China, Department of Bioengineering, Tatung Institute of Technology, Taiwan, Republic of China Bot. Bull. Acad. Sin. (1998) 39, pp. 93-97.

Ljunggren, H., et al. "The Role of Polygalacturonase in Root-Hair Invasion by Nodule Bacteria" Institut of Microbiology, Royal Agricultural College, Uppsala, Sweden J. gen. Microbiol. (1961), 26, pp. 521-528.

Pierpoint, et al. ScienceDirect—Physiological and Molecular Plant Pathology, vol. 36, Issue 4, pp. 267-362, Apr. 1990 Abstract attached.

\* cited by examiner

STORAGE-INDUCED PROMOTER

The invention concerns a promoter with an organ specific activity in plants, its application as well as transgenic plants.

According to Nilsson (2000), useful plants can be divided into three groups in view of storage life. Harvested crops of the first group, such as cabbage, broccoli, cauliflower, asparagus, and spinach, comprise leaves, sprouts, blooms, and buds. The plant parts of these plants have small water storage capability and quickly show a post-harvest senescence. Plants with fleshy fruits, such as tomato, pumpkin, and pears, belong to the second group. The fruits of these plants show a maturation and senescence during the storage. Biannual plants belong to the third group. Plants with a two-year life cycle, such as sugar beet, chicory, carrot, onion, or artichoke, develop a storage organ during the first year, which contributes to bloom and seed formation in the second year.

Storage organs are subject to numerous physiological changes after the harvest (postharvest), which influence the quality of the storage organs and the quantity of their contents. The physiological changes are on one hand the results of the mechanical treatment during the uprooting, such as injury and crushing, and on the other hand the consequence of storage and associated water loss, the consequence of a forced or natural dormancy or the result of a cold adaptation.

In order to influence the metabolism capacity of a storage organ after the harvest, designated processes, which preferably regulate the specific promoters, are required. Genes in the sprout of asparagus or the blooms of broccoli, which are activated after harvest, are known. However, this kind of gene is not known in the storage organs of plants and thus up to now there are no indications of suitable promoters.

The object of the present invention is, therefore, to provide such a promoter, with the help of which the metabolic physiological changes in the storage organs of plants after the harvest can be influenced.

The inventive solution of the above object is accomplished by a promoter with the features of claim 1.

First, some of the concepts used in this application will be explained in more detail:

In the sense of this invention, storage organs of a plant are such organs that serve to store carbohydrates such as sucrose, starch, or inulin and/or nitrogen compounds such as proteins or amino acids. A typical storage organ is, for example, the root or the hypocotyl. Sprout-like storage organs can be the tubers of potato, topinamburs, and halminternodien of sugarcane. Other storage organs are root tubers, which appear in yam, manioc, and sweet potato.

Biannual plants require a two-year development period for their life cycle. In the first year, a storage organ is developed. In the second year, the forming of blooms and seeds takes place by utilizing the reserve material of the storage organ.

A promoter is understood as a nucleic acid sequence, which controls the expression of a gene, if necessary, in dependence on endogenous and exogenous factors. These factors include, for example, inducers, repressors, and similar DNA-binding proteins, but also environmental influences. A promoter can comprise several elements. It includes, however, at least a regulatory element, which is responsible for the transcription of the gene under its control.

A promoter, which is activated in a storage organ after the harvest rather than before the harvest, and thus its activity is induced, shows, for example, in harvested roots an activity measurable through RNA-blots, which is detectable in comparable test conditions in not harvested roots as less than 20%, preferably as less than 10% and especially as less than 5%. The specificity can first occur with some delay after the uprooting and during the storage.

"Derivates" of a promoter are shortened or extended or in sections identical versions or homolog of the promoter with same or essentially same properties.

"Direct anti-fungal or anti-bacterial effect" means that the gene products act directly anti-fungal, whereby they, for example, dissolve cell walls or code for phytoalexin synthase or for a metabolite, which obstructively interferes in the fungal or bacterial metabolism.

"Indirect anti-fungal or anti-bacterial effect" means that the gene products activate the plant gene defense. These genes include, for example, resistance genes, components of the signal transduction (such as kinases, phosphatases), transcription factors or enzymes, which produce signal substances (such as ethylene forming, salicylic acid forming, or jasmonate forming enzymes, reactive oxygen species forming enzymes, nitrogen monoxide forming enzymes).

"Infection" is understood as the earliest point of time at which the metabolism of the fungus (or the growth of the fungus) is prepared for a penetration of host tissue, which includes the development of hyphae or the formation of specific infection structure such as penetration hyphae and appressors.

The expression "homology" means a homology of at least 70% at the DNA level, which can be determined according to known processes of, for example, computer-aided sequence comparison (see Altschul et al, 1990, Basic Local Alignment search tool, J. Mol. Biol. 215: 403-410).

"Complementary nucleotide sequence" means that in a double-stranded DNA, the second DNA strand, complementary to the first DNA strand, has nucleotide bases according to the base pairing rules, which correspond to the bases of the first strand.

The term "hybridize" means hybridization under normal conditions as described in Sambrook et al. (1989), preferably under the stringent conditions. Stringent hybridization conditions are for example: hybridization in 4×SSC at 65° C. and followed by multiple washing in 0.1×SSC at 65° C. for a total of 1 hour. Less stringent hybridization conditions are for example: hybridization in 4 x SSC at 37° C. and followed by multiple washing in 1×SSC at room temperature.

"Stringent hybridization conditions" can also mean: hybridization at 68° C. in 0.25 M sodium phosphate, pH 7.2, 7% SDS, 1 mM EDTA and 1% BSA for 16 hours followed by washing twice with 2×SSC and 0.1% SDS at 68° C.

The embodiments of the invention will be described in greater detail with the help of the figures.

The inventive promoter is active in the storage organs of plants, such as the root of sugar beet, carrot, and chicory or the tuber of potato, after the harvest. No or only very little activity is detectable in the storage organs or other organs before the harvest. This characteristic can be used to improve the metabolism of the storage organ after the harvest. Transgenic plants and parts of the plants such as seeds can also be produced by application of the promoter.

Preferably, the activity of the inventive promoter in the storage organ is measurable through RNA-blots, which is detectable in comparable test conditions before harvest of the storage organ as less than 20%, preferably as less than 10% and especially as less than 5%.

According to a further development of the invention, the promoter comprises:
  a) a nucleotide sequence according to SEQ ID NO: 1 or
  b) a nucleotide sequence according to SEQ ID NO: 2 or
  c) a nucleotide sequence according to SEQ ID NO: 3 or
  d) a nucleotide sequence according to SEQ ID NO: 4 or e) a nucleotide sequence according to SEQ ID NO: 5 or f) a nucleotide sequence complementary to the nucleotide sequences a) to e) or g) a nucleotide sequence that hybridizes with a nucleotide sequence according to a) to f).

Derivates of such promoter are also provided. Such derivates are defined above in more detail and also include DNA-fragments of the promoter, as are reproduced in the restriction map, or DNA-fragments, which are obtainable through application of not specifically named commercial restriction endonucleases.

The invention concerns then transgenic plants, which were transformed with the inventive promoter.

The invention also concerns the application of the inventive promoter or the derivates for production of a transgenic plant with one or more of the following properties:

a) improved carbohydrate metabolism in the storage organs after harvest b) improved nitrogen metabolism in the storage organs after harvest c) improved dry stress resistance and improved water status in the storage organs after harvest d) improved cold and frost tolerance of the storage organs after harvest e) increased resistance/tolerance of the storage organs against pathogens after harvest f) improved secondary metabolism in the storage organs after harvest The inventive promoter can thus be used to reduce or prevent the degradation of sugar in the harvested sugar beet and the accumulation of invert sugar. For that an invertase inhibitor gene in the harvested root is expressed and the activity of cellular invertases is inhibited.

The inventive promoter also can be used to achieve higher utilization of inulin and the production of long chain inulin molecules in the chicory root. For that the degradation of inulin in the harvested chicory is reduced or inhibited, in which the activity of fructosyl-exohydrolase in the root after the harvest is reduced through antisense or RNA deposit.

The inventive promoter can also be used to reduce the "cold-sweetening" of the harvested and stored potato tuber. For that the invertase inhibitor gene in the harvested tuber is expressed and the activity of cellular invertases is inhibited.

The inventive promoter can further be used to reduce the content of extractable "harmful nitrogen," such as amino acids, in the storage organs of the plants after the harvest. Higher concentrations of N-compounds in the storage organs often reduce the nutrition physiological value of the harvested products or make it difficult to isolate stored material such as sucrose from sugar beet roots. A reduction of extractable "harmful nitrogen" in the root can be achieved through an increased incorporation of amino acids in proteins in the storage organs with the help of the promoter. Proteins can, in contrast to amino acids, be cut down from the sugar beet during the sugar extraction and are thus not extractable.

The inventive promoter can also be used to improve the cold and frost tolerance of the storage organs. For that, for example, transcription factors for cold or frost tolerance or cold or frost protection protein are expressed through the promoter.

With the help of the inventive promoter, the sickness resistance of the harvested storage organs can be improved. Numerous in-ground reproducing fungi, such as the representative of the species *Fusarium* spp., or bacteria such as *Erwinia carotovora*, the exciter of the potato tuber wet rot, can infect the harvested storage organs. A fungus or bacterial resistance can be attained and the storage capability of the storage organ can be improved through combination of the inducible promoter with a gene, the gene product of which imparts a direct or indirect antifungal or antibacterial effect.

Finally, the inventive promoter can be used to improve the secondary metabolism of the storage organs. Potato tubers are the most important vitamin C source in central Europe. The vitamin C content of the tuber declines during storage. This vitamin reduction can be prevented or reduced with the help of the promoter.

FIGURES

FIG. 1 shows the induction of PHI (postharvest induced)—genes 7, 20, 153, and 227 of the sugar beet after the harvest of the beetroots through a RNA-blot experiment. The gene expression in the leaves and the roots of the sugar beet directly before the harvest (0 d) and then at different points in time after the harvest were analyzed. The roots were stored 1, 4, 7, 14, 21, 28, and 35 days at 17° C. and 1, 4, and 14 days at 26-28° C. In each case 10 μg total cell-RNA was separated per time instant in a denaturing formaldehyde-agarose gel and hybridized with the cDNA fragments of genes PHI7, PHI20, PHI153, and PHI227.

FIG. 2 shows the induction of the expression of the PHI (postharvest induced)—gene 5 in the root after the harvest of the sugar beet through a RT-PCR experiment. The PHI5 transcript is detectable only very weakly in the beetroots directly before the harvest (0 d) and very little in the leaves. In cDNA libraries, which were obtained from RNA of the roots stored 1, 4, 7, 14, 21, 28, and 35 days at 17° C. and 1, 3, 4, 7, and 14 days at 26-28° C., a strong PHI5 transcript is detectable. The detection of the expression of glycerinaldehyde-3-phosphate-dehydrogenase-gene (GAPDH) shows that same cDNA amounts were applied for the RT-PCR reactions.

Figure 1:
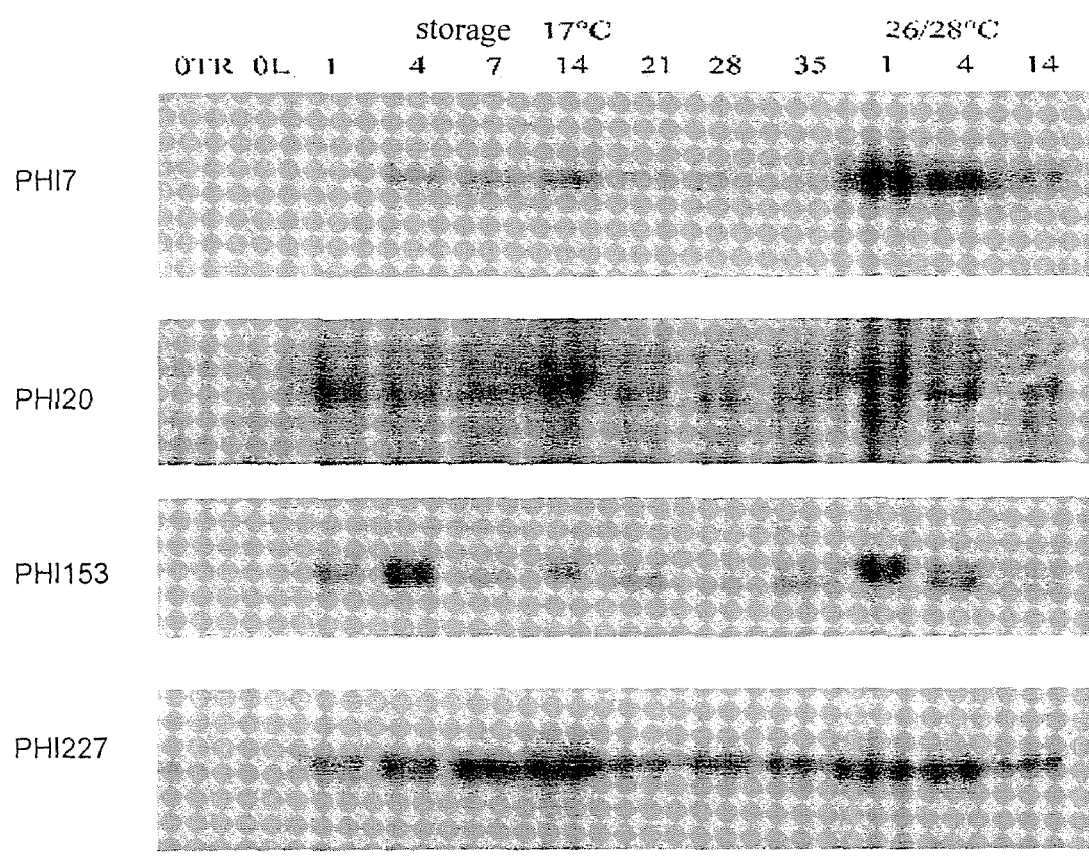

Determination of Induction of Gene Expression of PHI 7, 20, 154 and 227 in Harvested Roots of Sugar Beet Sugar beet seeds were sowed in the field in the spring and the sugar beets were cultivated according to the common agricultural practice. The storage roots of 24-week old plants were harvested in the fall and wounded superficially through a 30-second treatment in a commercial concrete mixer (Attika), in order to produce the wounding and crushing typical for a mechanical uprooting. The storage organs were then stored at 17° C. and 26-28° C. In each case 5 beets were retrieved from beets that had been stored at 17° C. for 1, 3, 4, 7, 14, 21, 28, 35, and 46 days after the harvest and at 26-28° C. for 1, 3, 4, 7, and 14 days after the harvest, and the total cell-RNA was isolated according to Logemann et al. (1987).

The analysis of the gene expression induced after the harvest is conducted through a RNA-Blot-Analysis according to Sambrook et al. (1989). In each case 10 µg total cell-RNA from leaves and roots, which are retrieved from the field directly before the harvest (0 d), and RNA from beets, which are stored 1-35 days long, are separated in a denaturing formaldehyde-agarose gel. The electrophoretically separated RNA was transferred to a Hybond N nylon membrane (Amersham Pharmacia Biotech, Freiburg). The radioactive marker of each 20 ng of the cDNA-clone of the postharvest induced (PHI) genes 7, 20, 153, and 227 was performed with 50 µCiP$^{32}$-dATP (6000 Ci/mMol, Amersham Pharmacia Biotech, Freiburg) with the help of Prime-It II Random Primer Kit (Stratagene GmbH, Heidelberg) according to the manufacturer's specification. The RNA-filters were then hybridized with the marked probe, washed, and exposed to an X-ray film.

The gene PHI7 was not expressed in the leaves before the harvest and only very little in the storage roots of the sugar beet. A strong induction of the gene PHI7 occurred in the roots after the harvest and during the storage. The induction was higher at 28° C. than at 17° C. (FIG. 1).

The gene PHI20 was expressed only very little in the leaves and in the root of the sugar beet before the harvest. A strong and long lasting induction of the gene PHI20 occurred in the storage organs after the harvest and during the storage. The induction at 17° C. was comparable with that at 28° C. (FIG. 1).

The gene PHI153 was expressed in the leaves and in the storage root of the sugar beet before the harvest. A strong induction of the gene PHI153 occurred in the root after the harvest and during the storage. The induction at 28° C. was comparable with that at 17° C. (FIG. 1).

The gene PHI227 was expressed only very little in the leaves and in the root of the sugar beet before the harvest. A strong induction and a high, long lasting expression of the gene PHI227 occurred in the root after the harvest and during the storage. The induction at 17° C. was comparable with that at 28° C. (FIG. 1).

Determination of the Induction of Gene Expression of PHI5 in Harvested Roots of Sugar Beet A RT-PCR experiment was carried out for determination of induction of gene expression of PHI5 in harvested roots of sugar beet. A cDNA library was produced with the help of RevertAid H Minus cDNA Synthese Kit (MBI Fermentas) according to manufacturer's specification from in each case 5 µg total cell-RNA of leaves and roots, which are retrieved from the field directly before the harvest (0 d). Further cDNA libraries were produced in each case from RNA, which had been isolated from beets stored at 17° C. for 1, 3, 4, 7, 14, 21, 28, 35, and 46 days and at 26-28° C. for 1, 3, 4, 7, and 14 days.

The expression of the gene PHI5 was determined with the primer PHI5-1 with the nucleotide sequence according to SEQ ID NO: 6 (GTG CAA GGA TTC TGG CAC CCG TCG GTG G) and the primer PHI5-2 with the nucleotide sequence according to SEQ ID NO: 7 (GTA TGG GCC GCG GCA GAT CCA GGT AGC G) with the help of taq-polymerase (Q-Biogene) according to manufacturer's specification. For control purpose, the expression of the gene glycerinaldehyde-3-phosphate-dehydrogenase (GAPDH) was detected through the primer GAPDH-1 having the nucleotide sequence according to SEQ ID NO: 8 (ATG TTT AAG TAC GAC AGT GTT CAC G) and GAPDH-2 having the nucleotide sequence according to SEQ ID NO: 9 (ATG TGA AGG TCT GAC TTG TAT TCG T), in order to ensure that same cDNA amounts had been used for the RT-PCR.

Figure 2:
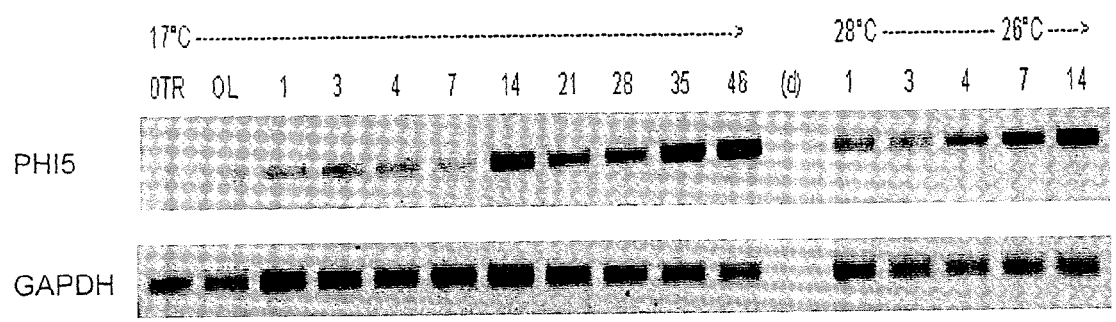

The RT-PCR analysis shows that the gene PHI5 was expressed very weakly in the leaves and very little in the roots before the harvest (0 d). The beets stored at 17° C. and 28° C. showed a strong expression and thus an induction of the gene PHI5 in the storage organ after the harvest and during the storage (FIG. 2). The beets stored at 17° C. showed after 1-7 days after the harvest a clearly less expression of the gene PHI5 as during the days 14-46. The beets stored at 26-28° C. showed at day 1-7 after the harvest a clearly less expression of the gene PHI5 as during the days 4, 7, and 14. The expression of the GAPDH gene was the same in all samples (FIG. 2). This result showed that the expression of the PHI5 gene after the harvest was induced. However, the induction during the first days of storage, which was physiologically a direct result of mechanical uprooting, was clearly less than during the phase of later storage and the associated physiological changes.

Classification of PHI Promoters

The promoters PHI5, PHI7, PHI20, PHI153, and PHI227 were all induced after the harvest in the root of the sugar beet through the harvest process and the subsequent storage of the storage organ (FIGS. 1 and 2). Beside this general property of post-harvest induction, the five promoters differ from one another in view of the root activity before the harvest, the influence of the uprooting and the storage on the kinetics of the induction and the influence of the storage temperature on the strength of the promoter induction. These differences allow the formation of four subclasses of post-harvest induced promoters (Table 1).

The promoter PHI153 belongs to the first subclass of PHI-promoters, in which no gene transcript in the storage organ before the harvest is detectable.

The promoters PHI20 and PHI227 belong to the second subclass of PHI-promoters, which showed a weak activity in the storage organ before the harvest, the induction of which was of the same strength after the harvest both at the lower temperature (17° C.) and at higher temperature (28° C.) and thus temperature independent.

The promoter PHI7 belongs to the third subclass of PHI-promoters, which showed a weak activity in the storage organ before the harvest, the induction of which was clearly stronger at the higher temperature (28° C.) than at the lower temperature (17° C.).

The promoter PHI5 belongs to the fourth subclass of PHI-promoters, which showed a weak activity in the storage organ before the harvest, the activity of which was moderate as a result of the mechanical treatment after the harvest and strongly increased during the storage.

Fusion of the Promoters PHI5, PHI7, PHI20, PHI153, and PHI227 With the Luciferase Gene From *Photinus pvralis*

In order to determine the activity of the promoters PHI5, PHI7, PHI20, PHI153, and PHI227 in sugar beets, the promoters were translationally fused with the luciferase gene from *Photinus pyralis* and transformed in the sugar beets. For that the promoter PHI5 as HindIII-BspHI fragment and the promoters PHI7, PHI20, PHI153, and PHI227 as HindIII-NcoI fragment are cloned in the binary vector pGPTV-kan linearized with HindIII-BspHI or HindIII-NcoI (Becker et al., 1992).

Figure 3:
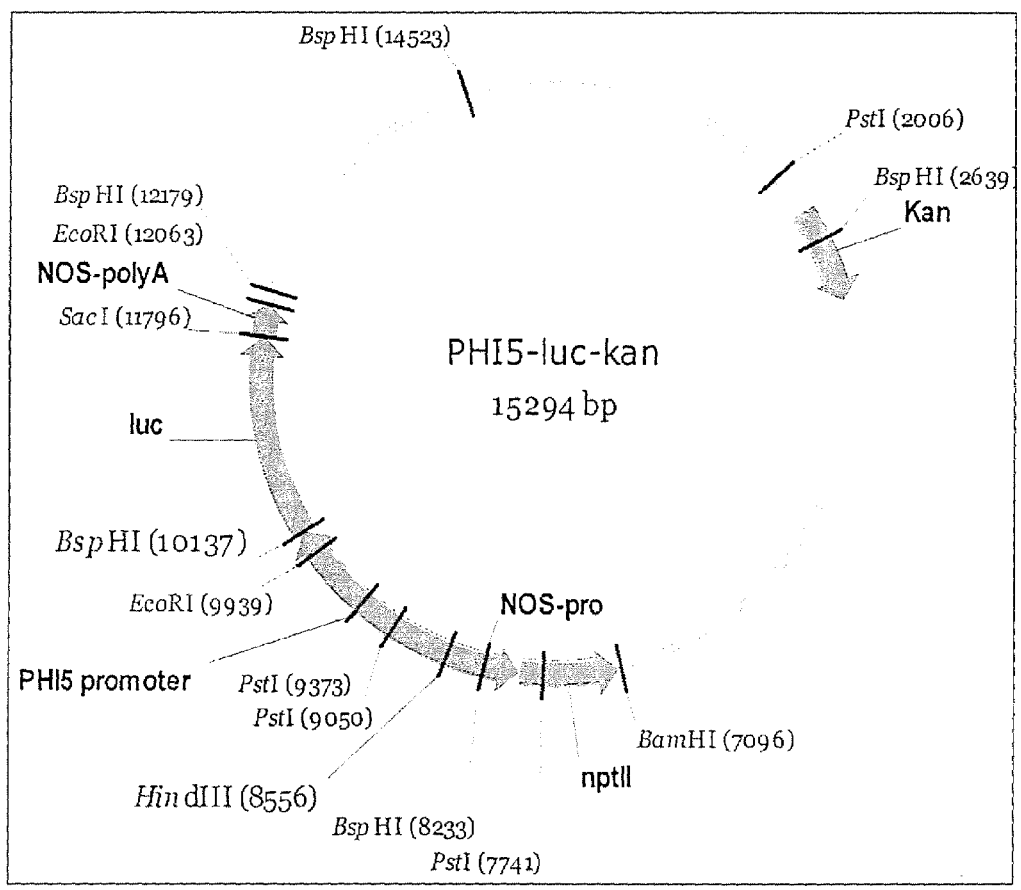
FIG. 3 shows the reporter gene vector PHI5-luc-kan with a translational fusion between the promoter PHI5 and the luciferase gene from *Photinus pyralis*. The promoter PHI5 in the vector PHI5-luc-kan comprises the nucleotide positions 1-1587 of the nucleotide sequence SEQ ID NO: 1 and can be isolated from the vector with the help of HindIII and BspHI and combined with other genes.
Figure 4:
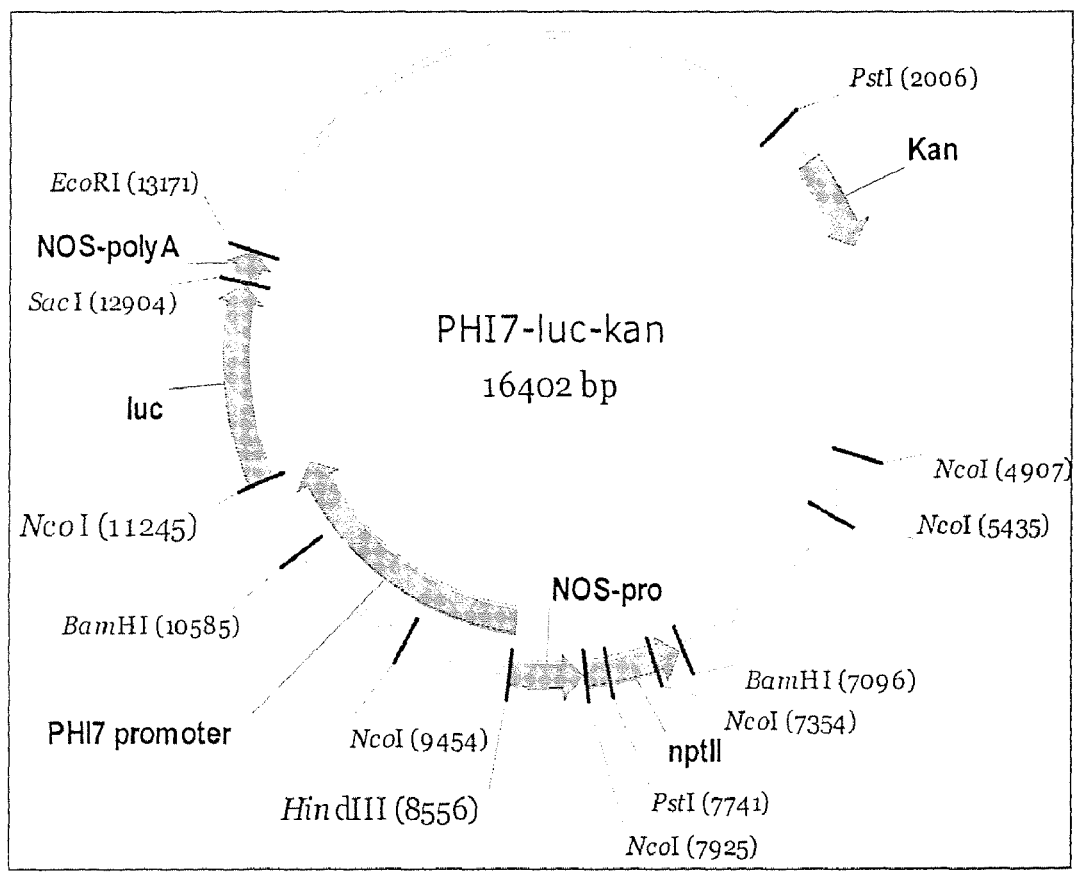
FIG. 4 shows the reporter gene vector PHI7-luc-kan with a translational fusion between the promoter PHI7 and the luciferase gene from *Photinus pyralis*. The promoter PHI7 in the vector PHI7-luc-kan comprises the nucleotide positions 1-2695 of the nucleotide sequence SEQ ID NO: 2 and can be isolated from the vector with the help of HindIII and NcoI and combined with other genes.
Figure 5:
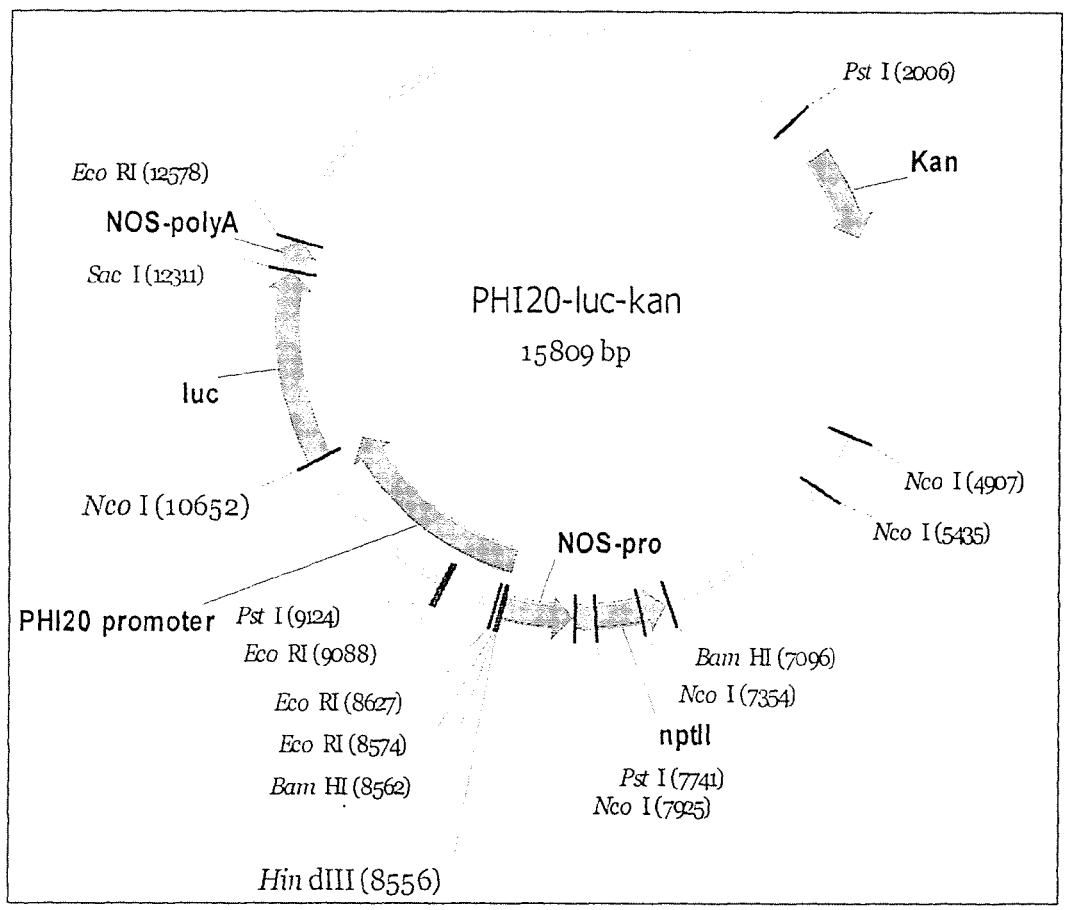
FIG. 5 shows the reporter gene vector PHI20-luc-kan with a translational fusion between the promoter PHI20 and the luciferase gene from *Photinus pyralis*. The promoter PHI20 in the vector PHI20-luc-kan comprises the nucleotide positions 1-2102 of the nucleotide sequence SEQ ID NO: 3 and can be isolated from the vector with the help of HindIII and NcoI and combined with other genes.
Figure 6:
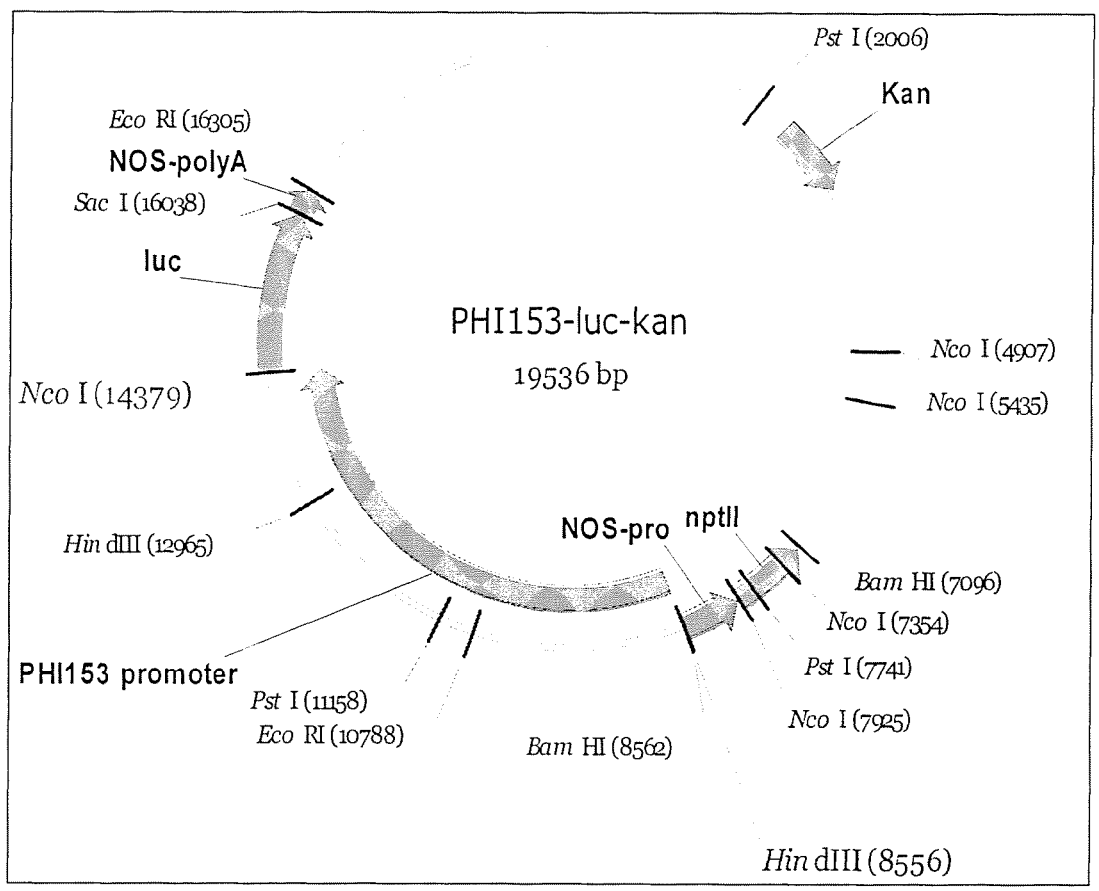
FIG. 6 shows the reporter gene vector PHDI153-luc-kan with a translational fusion between the promoter PHI153 and the luciferase gene from *Photinus pyralis*. The promoter PHI153 in the vector PHI153-luc-kan comprises the nucleotide positions 1-5829 of the nucleotide sequence SEQ ID NO: 4 and can be isolated from the vector with the help of HindIII and NcoI and combined with other genes.
Figure 7:
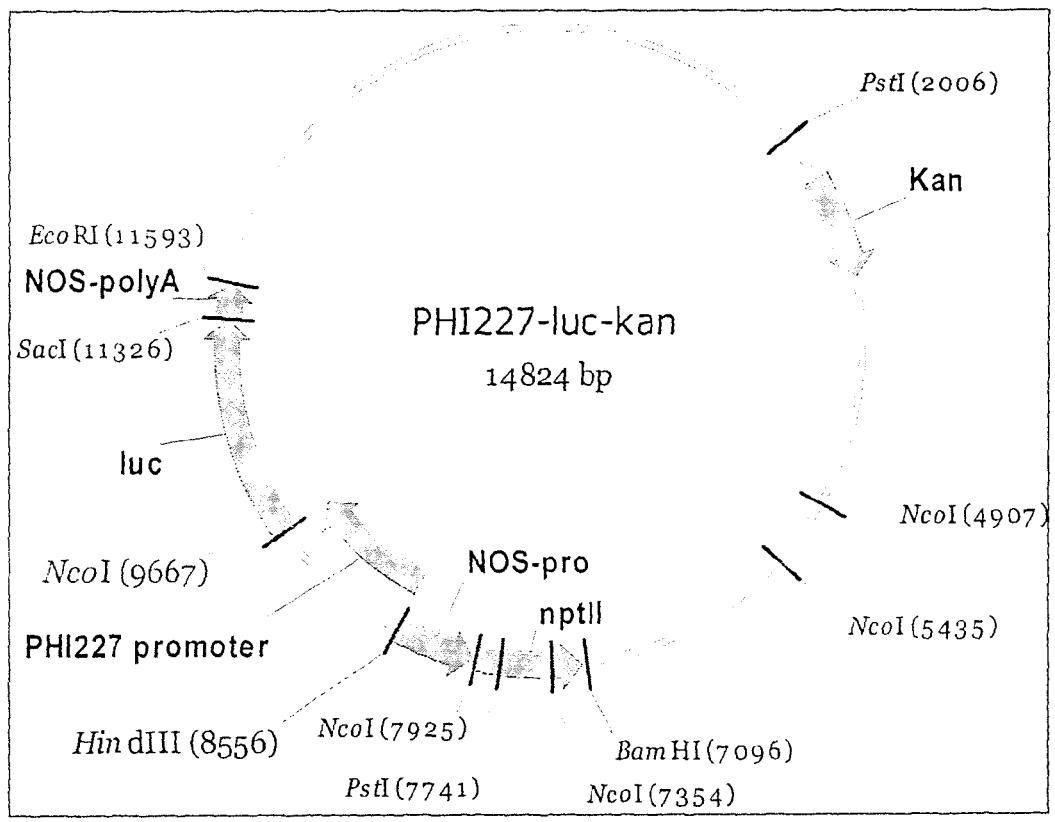
FIG. 7 shows the reporter gene vector PHI227-luc-kan with a translational fusion between the promoter PHI227 and the luciferase gene from *Photinus pyralis*. The promoter PHI227 in the vector PHI227-luc-kan comprises the nucleotide positions 1-1117 of the nucleotide sequence SEQ ID NO: 5 and can be isolated from the vector with the help of HindIII and NcoI and combined with other genes.

The developed vectors carry the designation PHI5-luc-kan (FIG. 3), PHI7-luc-kan (FIG. 4), PHI20-luc-kan (FIG. 5), PHI153-luc-kan (FIG. 6), and PHI227-luc-kan (FIG. 7). The binary vectors were transformed in the *Agrobacterium tumefaciens* strain C58C1 with the resident plasmid pGV2260 through a direct DNA-transformation process (An, 1987). The selection recombinant *A. tumefaciens*-clone was accomplished under the application of antibiotic kanamycin (50 mg/l).

The transformation of the sugar beets was accomplished according to Lindsey et al. (1991) under the application of antibiotic kanamycin. The transgenicity of the plants was inspected through PCR. The application of the primer having the nucleotide sequence according to SEQ ID NOs: 8 and 9 (GTGGAGGGCTATTCGGTA and CCACCATGATAT-TCGGCAAG) led to the amplification of a 553 by large DNA fragment from the nptII gene. The PCR was carried out under application of 10 ng genomic DNA, a primer concentration of 0.2 μm at an annealing temperature of 55° C. in a Multicycler PTC-200 (MJ Research, Watertown, USA).

The luciferase gene of the vector PHI5-luc-kan (FIG. 3) can be released as BspHI-SacI fragment and the luciferase gene of the vectors PHI7-luc-kan (FIG. 4), PHI20-luc-kan (FIG. 5), PHI153-luc-kan (FIG. 6), and PHI227-luc-kan (FIG. 7) as NcoI-SacI fragment and can be replaced by another expressing gene such as an invertase inhibitor gene. The expressing gene should be as NcoI-SacI fragment. Alternatively, the PHI5 promoter can be isolated as HindIII-BspHI fragment and promoters PHI7, PHI20, PHI153, and PHI227 as HindIII-NcoI fragment and inserted in the suitable expression vectors.

Determination of PHI5 Promoter Activity in Stored Roots of Sugar Beet

Transgenic sugar beets, which had been transformed with the reporter gene construct PHI5-luc-kan, were applied under green house conditions. 20-week old plants were harvested and the roots were stored for six weeks. The activity of the promoter was analyzed in the roots and the leaves before the harvest and weekly in the stored roots through a reporter gene measurement.

The *Photinus pyralis* luciferase activity was determined with the Luciferase Assay System (Promega, Mannheim, Germany) in a Sirius Luminometer (Berthold Detection System GmbH, Pforzheim, Germany) according to manufacturer's specification. The weight of the tissue sample is first determined for the preparation of an enzyme extract suitable for the measurement. The sheet samples were homogenized under the addition of sea sand with the 10× volume (v/w) on Passive Lysis buffer (PLB) in a mortar and the root samples in a commercial kitchen appliance (Warring blender). The liquid supernatant transferred to a 1.5 ml Eppendorf vessel and centrifuged 5 min at 4° C. and 20 000 g. The clear supernatant was removed and in each case 10 μl Roh extract is added for the *Photinus* luciferase activity measurement.

While the PHI5 promoter was only weakly active in the roots and leaves before the harvest, the promoter activity in the harvested and stored roots strongly or very strongly increased in 8 independent transformants. The PHI5 promoter activity was strongly induced according to the result of the reporter gene study in agreement with the RT-PCR result after the harvest in the root of sugar beet.

Transgenic Plants With Special Properties transgenic plants with special properties can be produced with the inventive promoter:

a) improved carbohydrate metabolism in the storage organs after harvest b) improved nitrogen metabolism in the storage organs after harvest c) improved dry stress resistance and improved water status in the storage organs after harvest d) improved cold and frost tolerance of the storage organs after harvest e) increased resistance/tolerance of the storage organs against pathogens after harvest f) improved secondary metabolism in the storage organs after harvest Improved Carbohydrate Metabolism in the Storage Organs After Harvest The carbohydrate metabolism of storage organs of plants can be variedly improved through the application of the inventive promoter. Mechanical treatment during the uprooting and the physiological changes during the storage of sugar beets and carrots result in post-harvest strong hydrolysis and depletion of sucrose and the accumulation of invert sugar (Burba 1973, Smed et al., 1996, Galindo et al., 2004). The sugar losses in the magnitude of 0.01-0.025% per day reduce the isolatable sugar amount from sugar beets. The invert sugar formation leads to technological difficulty during the industrial sugar isolation (Burba, 1976).

The inventive promoters can be used to reduce the sucrose hydrolysis and invert sugar formation. For this suitable invertase inhibitor genes are strongly expressed post-harvest or the expression of the endogenous sucrose synthase genes or invertase genes are reduced through an antisense or RNA deposit.

The inventive promoters can also be used to achieve higher utilization of polyfructan such as inulin and the production of long chain inulin molecules in the chicory root. For that the degradation of inulin in the harvested chicory is reduced or inhibited, in that the activity of the fructosyl-exohydrolase in the root after the harvest is reduced through antisense or RNA deposit.

Improved Nitrogen Metabolism in the Storage Organs After Harvest

The inventive promoter can be used to reduce the content of extractable "harmful nitrogen," such as amino acids, in the storage organs of the plants after the harvest. Higher concentrations of N-compounds in the storage organs often reduce the nutrition physiological value of the harvested products or make it difficult to isolate of stored material such as sucrose from sugar beet roots. A stronger incorporation of the amino acids in the proteins in the storage organs is achieved through stronger expression of corresponding enzymes, transcription factors, storage proteins and similar. Proteins can, in contrast to non-extractable amino acids, be precipitated from the sugar beet during the sugar extraction.

Increased Tolerance of the Storage Organs Against Soil-Reproducing Pathogenic Fungi and Bacteria The inventive promoter can also be used, in combination with a gene or a gene combination, to develop a direct or indirect antifungal effect in the storage organs of plants. The antifungal effect leads to a higher fungus resistance or tolerance after the harvest and during the storage.

The promoter is thus translationally or transcriptionally fused with genes of pathogen resisting organism, the gene products of which have a direct or indirect antifungal or antibacterial effect. The promoter-gene combinations are cloned in the binary transformation vector pGPTV and transformed in the sugar beets, carrots or potato through *A. tumefaciens* mediated transformation. The transgenicity of the plants is, as described, inspected through PCR and the expression of the gene in the roots or tuber is verified through RNA-blot studies. The higher fungus or bacterial resistance of the storage organs is observed by resistance test.

Surprisingly, the post-harvest induced expression of pathogen resistant genes did not lead to dwarfism or yield decrease often observed by a constitutive expression during the vegetative development of plants (Heil and Baldwin, 2002).

REFERENCE

Altschul, S. F. et al. (1990). Basic Local Alignment Search Tool, J. Mol. Biol. 215: 403-410

An, G. (1987). Binary Ti vectors for plant transformation and promoter analysis. Methods Enzymol. 153, 292-305.

Becker D, Kemper E, Schell J, and Masterson R. (1992). New plant binary vectors with selectable markers located proximal to the left T-DNA border. Plant Mol Biol. 20(6):1195-7.

Burba, M. (1976). Atmung and Saccharosestoffwechsel lagernder Zuckerrüben. Zeitschrift für die Zuckerindustrie 26: 647-658.

Galindo, F. G., Herppich, W., Gekas, V., and Sjöholm, I. (2004). Factors affecting quality and postharvest properties of vegetables: Integration of water relations and metabolism. Critical Reviews in Food Science and Nutrition 44:139-154.

Heil, M. and Baldwin, I. T. (2002). Fitness costs of induced resistance: emerging experimental support for a slippery concept. Trends Plant Sci. 2002 Feb;7(2):61-7.

Lindsey, K,. Gallois, P., and Eady, C. (1991) Regeneration and transformation of sugar beet by *Agrobacterium tumefaciens*. Plant Tissue Culture Manual B7: 1-13; Kluwer Academic Publishers.

Logemann, E., Parniske. M., Hahlbrock, K. (1995). Modes of expression and common structural features of the complete phenylalanine ammonia-lyase gene family in parsley. Proc Natl Acad Sci USA. 1995 92(13):5905-9.

Nilsson, T. (2000). Postharvest storage and handling of vegetables., In Fruit and Vegetable Quality (an integrated view), Seite 96-121. Herausgeber Shewfew, R. L. and Bruckner, B., Technomic Publishing Inc.

Sambrook, J., Fritsch, E. F., and Maniatis, T (1989). In Molecular Cloning, A Laboratrory Manual (Cold Spring Harbor Laboratory Press, New York).

Smed, E., Augustinussen, E., and Stensen, J. K. (1996). Loss of sugar in injured sugar beet losses from lifting , storing and washing. Proceedings of the 59th IIRB Congress, 533-545.

The invention claimed is:

1. A promoter comprising
the nucleotide sequence according to SEQ ID NO: 5 or
the nucleotide sequence complementary to the nucleotide sequence of SEQ ID NO: 5.

2. The promoter according to claim 1, wherein the activity of the promoter in the storage organs post harvest is measurable through RNA-blot, which in comparable test conditions prior to the harvest of the storage organs is detectable at less than 20% of the activity post harvest.

3. The promoter according to claim 1, wherein the activity of the promoter in the storage organs post harvest is measurable through RNA-blot, which in comparable test conditions prior to the harvest of the storage organs is detectable at less than 10% of the activity post harvest.

4. The promoter according to claim 1, wherein the activity of the promoter in the storage organs post harvest is measurable through RNA-blot, which in comparable test conditions prior to the harvest of the storage organs is detectable at less than 5% of the activity post harvest.

5. A vector or mobile genetic element including the promoter according to claim 1.

6. A plant or prokaryotic host cell including the promoter according to claim 1.

7. A transgenic plant or parts thereof transformed with a nucleic acid comprising the promoter according to claim 1.

8. A plant or prokaryotic host cell including the vector or genetic element according to claim 5.

9. A transgenic plant or parts thereof transformed with the vector or genetic element according to claim 5.

10. The transgenic plant according to claim 9 or 7 wherein said plant is *Beta vulgaris*.

11. A method for producing a transgenic plant, said method comprising transforming a plant with the promoter according to claim 1 fused with a coding sequence for producing a transgenic plant with one or more of the following properties:
   a) improved carbohydrate metabolism in the storage organs after harvest,
   b) improved nitrogen metabolism in the storage organs after harvest,
   c) improved dry stress resistance and improved water status in the storage organs after harvest,
   d) improved cold and frost tolerance of the storage organs after harvest,
   e) increased resistance/tolerance of the storage organs against pathogens after harvest; or
   f) improved secondary metabolism in the storage organs after harvest.

* * * * *

UNITED STATES PATENT AND TRADEMARK OFFICE
CERTIFICATE OF CORRECTION

| | | |
|---|---|---|
| PATENT NO. | : 8,093,457 B2 | Page 1 of 1 |
| APPLICATION NO. | : 11/720252 | |
| DATED | : January 10, 2012 | |
| INVENTOR(S) | : Reinhard Hehl et al. | |

It is certified that error appears in the above-identified patent and that said Letters Patent is hereby corrected as shown below:

On the Title Page:

Line (73) Assignee: should read --

KWS SAAT AG, Einbeck (DE); Suedzucker AG, Mannheim (DE)

Signed and Sealed this
Twenty-ninth Day of May, 2012

David J. Kappos
*Director of the United States Patent and Trademark Office*

SEQUENCE LISTING

```
<160> NUMBER OF SEQ ID NOS: 11

<210> SEQ ID NO 1
<211> LENGTH: 1587
<212> TYPE: DNA
<213> ORGANISM: Beta vulgaris
<220> FEATURE:
<221> NAME/KEY: misc_feature
<222> LOCATION: (1584)..(1586)
<223> OTHER INFORMATION: Tranlations start ATG

<400> SEQUENCE: 1
aagcttttct ttattgaata tacatataac accgtgcaca tacagatagc aacgatttga      60
aggctggtgg tagtaaagta tctataagta aaaggaaagc aatccaagta ctttgttttg     120
aaagccctcg atctagccta tagaaaaggt agttgactta cttagttaaa gcaaagcatt     180
aagaaaggaa tttgattgat atggatactt tttttgaaaag tgagacactt tctatgccga     240
gtgtaaattc gataccctcct tgcttccctt aaagctcaac ctccccatgg tatgccctcc     300
tctggattgg gtagtccaac accctgaagt taaagaataa tggttaaaca tttctgattt     360
taaaggggat tacctataaa ttcaataagt ggtctaatac atgaccgtta ttgtcttta     420 agttctggta acattaagaa tttctttatt tactttggta agttcgagga tagtttaagc     480
cttaaaaagg ctgcagacct gtgcgaggta atgaacaagc tccagagatt tttcatttaa     540
ttttcatggc tgatttgtca tttgtatatt taatttcaga tttgtaattt ttgtatgtag     600
attatatttt ttttagtttg gaattaatag ggatgtattt cactgcattt ttagttgtat     660
gccagtgggt atttttgatt ttagtttggg atgtatgtgg ctgcaaacat gtgtgtattt     720
tggtggaaag tggtggaaat gtgggggggga ggggtagtgt agacctgcaa atgtgattgt     780 tgcttttttgt tttggtagtg cagacctata ggcctgcagg tctgtaactt tttttttcgac     840 atacatttca acaaactgat gtgatttttc ttaagaaccg catcaataaa tcatttactg     900
```

```
attcgatttt tgatcggatc agtaaatgat tgggagagct gctgcgagcc cacctgatgc      960
ggaccaaccc aattttgacc acatcaagat gggcttttt ccactaatgt aagatcatat     1020
attatctaga agtgagcccc ttaacttgta aaatgaccct tttcacttac aaagtaatta    1080
acccttaaaa aaaataaagt gaggtggtct taccataatt ttattgtaag acttccttgc    1140
tcaagatcta ctaataatga gaatatgcca agaaaaaaac gactatgaga cgattccata    1200
atcctcgaaa gttcttaaaa tcttaaacta aaacatttag gaaaaaaatt ctgaaaaaat    1260
ttcaacgtaa cctacaaagc tccttcaaac aactatgttt taatcagcac gaaacccttta   1320 ttaaacctca ttcagtcatc cccttctaac aagatagtcc tcttacagaa taaaaataca    1380
caagaattca tcctcatccc tcgtcagcaa tatgccaaat ctatctttga caattctaca    1440
caatcaaaca atgaatattg cccgaaaaca aagcaaagaa gatcaagtta gccgcctaca    1500
acccctattt aaaccccct catcatctca acatttccac acacaaaaac catactacta    1560
aatcatcatc ataatataca atcatga                                        1587
```

<210> SEQ ID NO 2
<211> LENGTH: 2695
<212> TYPE: DNA
<213> ORGANISM: Beta vulgaris
<220> FEATURE:
<221> NAME/KEY: misc_feature
<222> LOCATION: (2692)..(2694)
<223> OTHER INFORMATION: Translations start ATG

<400> SEQUENCE: 2

```
aagcttctcg agaaagccat ctaaaaggag taggagagag agaggaaggc attgacgagt      60
tgagaactga gttggatcgt tcggatttct tcttcttcct gagcgtactt ttaacacccg     120
ccattactcg ttagcaatga agaagagaag tagcacgagt ttcttacatc ttgaaagaga     180
gtcaatggtt ttggttggtg cgttacgaac gagatgggat gggactatgg tctatgggag     240
aatggtcaac tagacccaaa tgctaatgcg atggattagg ttatttaggt cccgttcttt     300
ttcactaaga taaatgaac tgaaataaat tgaactaata gaaactatat tatagagaga     360
tattaaacta aattgaactg aaattaactg gctgaaaata aatccaaaat aacagagcct     420
taaccttagt ggtgaagtgg cggaatgaag atttttgtat taaggtctaa ctcagacagt     480
tagagcttcc gtcacgtaat caagagactg gaccaatgat aatcaaacgt ctcgcgccat     540
tgctcttgaa caagatttca cacatgtgaa gatagcggat tttcgaaaca catcggcata     600
ttgccaaggc cttaaaaccc tctctgatta gttaaatagt gtgagggacg tgtgtggcggt    660 gtctggtagt cgccttctcc tacacatggt ggttgggttt accgaggcct acaagggtgt     720
tggcaccatg attcggcaaa gtaaaccttt gccttccttc attaaagcac gttcgagcct     780
tctccctaaa ggaaatgtca atgcttgatg aatcaccgtt ggctatggtg gtgactcaga    840
acgaggatgg cgcatctgac tccttttctc atactcgaca tggtaagaaa gtatggaacc     900
atggctcgca caataatcat aagcaatctg gtggtggtcg cagcgatgga agtgtcgtg      960 gtggtggtgt tcgtgtccgc ggtggtcacg gtggaggcgc cggacaacaa caaccttagg    1020
ccgccacccc tccttggtcg tatgcagctg gtagttggtg ttgggtgccc caacagtggg    1080
tagttccttt ttacccacac tcaacagtgg gcagttccgt tattgggcca tatccaaata    1140
gtctagtaag tcaacgaggt ttgagtatgc cgggcggctg ggcctgcgtg catctcaagt    1200
ctatatggtt gcatatgttc ctactgatct tacttttgca tttcacacta tgacacttgc    1260
ttctccgaac tccaattggt atatggacat tggtgctacc tcacatatga cctccacacc   1320
```

```
aagtaatctc acgtcttatt ttaatttgag caatacaaat ggtattacta tttgtaatgg    1380
tctaacaatt ccgatttgtg gttatggtaa aaaaattccg attttttgtgg ttatggtcat   1440 tcacatatat cttcttttcac aaaccaaaca gaggaaagtg aagaaaataa ttttactcaa   1500
aaatattttc cttccaatcc gtcaaaaaga atctcgtgat tccttaacaa aaaaaaaaaa   1560
attaaaaaaa aaacaaaggg aaaaatagtg tattgtaggg catacgtaga ataatacggt   1620
tgactagaga tggcaatgga tcatgcaacc gacccattta tatgggtctg agtctagata   1680
ttttagaccc aatgggtccg ggtcgggtct gggtccacat atgttaggca ccggcttgat   1740
tcgcagacct atttacatat tagaattttt tttacctata ctctaaagtt ttattagttg    1800
tgattttatt aactcgttag tgttgtaact ccatataaga cttgtaactt tgtcaattgt    1860
aacattttat gatttcatga gttaatttttt aaaattttgt ttagataata cttaaaccag   1920
ggatgcaaga cctatatagt agggcagaat ttttttaatta catatattca aaaatgtaat   1980
gaaaacttag aattatgatg gacacattta ggacccaaat aggacccgtg gatccgctag    2040
attcaccgaa tctggaactg ggtctgaaaa attttgaccc aacgaattta aaatggatat    2100
gaatctgtaa aaaaataaac gggcatgggt tcagttgaac tcgccgcaga ccctccccat    2160
tctacgttga cggtcacgga tggtgcatga aagggggtcaa cgatcaatgt gagagcaacc   2220
caagcgtttg gtttcccaat ttccactatt ttcgcaaatc atttcactgt aaacatttaa    2280
gaaaaaacgg tgaacattcc agactcaact agacaactag ttggcttgaa ccttctcgaa    2340 ttatttttctt aacaaaaaga aagttcatcc tcaaacgcac agtttcatat ccataacgcc   2400
acaacacaca aaaaacgcgt cgtttcctca caacaatttt taaaaaaccc caccaaaaat   2460
aatactagta taacacaact aagaaacaat tctagagaag agtagaactc tccagaacaa    2520
agaagcaaga aaatagctct cctctctgct ataaaaacct cttcctgtct ttctcgcctt    2580
catcaccatt ctctctctaa agcaatctaa gcaaacacca aagcaatcaa tccacattat    2640
ctcttctata atcgcgaaat ttctaggtta ttttttttctg aaggtgcatc catgg        2695
```

<210> SEQ ID NO 3
<211> LENGTH: 2102
<212> TYPE: DNA
<213> ORGANISM: Beta vulgaris
<220> FEATURE:
<221> NAME/KEY: misc_feature
<222> LOCATION: (2099)..(2101)
<223> OTHER INFORMATION: Translationsstart ATG

<400> SEQUENCE: 3

```
aagcttggat ccatcgatga attcggcgcg ccactagtat attggggttg aggagacaac      60
cattaacaaa cgaattcaaa attttaattc ttcttatatt tatatatgta tttctgtttc     120
atcttcattt cttttttttgc acaatcctat taaaatctca tattcaatga aattcggcta    180
attcaatcaa gagatattca acactatgtt caattcctcc tcaatgtatg cacccaactc    240
caagcgatcc aactaataag gtctgttcgt aatcattttt tgttttcaat tttctgtttt    300
tctgaaaact aaaaacaaaa aacagaatac tagaaaagt gattttcaat cacatttag     360 ttatcagttt tcagaatcat catgtttttca ataagttcca ttattttttg gttcattata    420
ggacatatag taatattata tgacttctaa aaacaaaaaa ctgaaaacca cagtgataac    480
gaccgggccc taagttacga gtttacaata ggcaacaacg caacattaat tagaattcac    540
ccggttatat catatacccg cgtgctgcag gtggcttaca cttatatatg atatagccgt    600
tcgagggcac cttaaggctc accctccttt cgaagacttc atgcatgcgc attcaggaat    660
```

| | |
|---|---|
| ccatcgcacc atcaaggctc atcgaacacc aggggcagat gtacattgta ctgtgcttag | 720 |
| tgcggttagt tgacctcact taaatttgaa aacttcggga acttttctta cataatttga | 780 |
| gattttttttg gatatttttct agtaaaattg attgtttgaa cctactaaaa aatagtaatt | 840 |
| ttatttcgac ctcactgaat acatattcta gatccatcaa tgaacaaaaa cgccacgcat | 900 |
| cgagtcagag gaaggatctg ctgctatagt gttattgtct cttgctcgct agaacattgt | 960 |
| ccacataaaa agcatcgtcg acgtccatca catgcatgct gctcatggag cctacctaat | 1020 |
| tgttgcggat gctactcagc cctccatagg aagtggctta gttgaagggg gacctaggtc | 1080 |
| atgaactacg ttattatcag ttcacgtgct agtacttgag ataatgctac atggacataa | 1140 |
| gtccataaca catgataaat caatcgtacg tgaaagggtg gcggctacct ttttctaatt | 1200 |
| gtatttgtgt cactactttt tctcttctgc tcatcatcat atcgtaagtc aaaaattcgt | 1260 |
| gatgactaat gtacgtctag tcatgcaagt ttattaatta ggaaaaatta ttttttgataa | 1320 |
| gataacttttt gcgcgttttt cttaaattaa gttaattttt tgattaaata tgaataaatt | 1380 |
| aatttttatat ctacttttgt tataaatgag ttaaatcaca atgtcatcct attaaaatgt | 1440 |
| gacacgtatc atactttcaa tgttatgaag tagatacaaa gttaacttat taatcagaag | 1500 |
| attaccttat taaaaacaat ttttcttatt aactgtgaac gttattatta atacataata | 1560 |
| gtaaacatta ttatcatgtg aaatcgtatt aaatttattt caattagatt taagttaata | 1620 |
| actttaattt atataatttt attaataaaa attaaagata tatattaaca gtcaaataaa | 1680 |
| cgtattaaaa accattaaaa aaaagataaa ctaatagaat ctccaaggtg gtaaagtcta | 1740 |
| accaacgacg aataaacaat tccattatac tagcacgata gataaggtta agttaccata | 1800 |
| cttattcatg tgatgtgagt gacatgtgac taaagttacc atgttggcac accatgctac | 1860 |
| gtagatttag aaaagtcata cacccgacaa tcaactttaa tttggttgca tgattaaaac | 1920 |
| gacgccatta gaaaaaaaat ctaagcaaca tatagtcata tacctccaaa ctttgcattg | 1980 |
| attgggttca ctataaataa agaaaagcct ctcactcata aatttcatca aatcttgctt | 2040 |
| gaaaataaat ccattaaccct aattgagatt cttatagcaa gttttgcata tatagaccat | 2100 |
| gg | 2102 |

<210> SEQ ID NO 4
<211> LENGTH: 5829
<212> TYPE: DNA
<213> ORGANISM: Beta vulgaris
<220> FEATURE:
<221> NAME/KEY: misc_feature
<222> LOCATION: (5826)..(5828)
<223> OTHER INFORMATION: Translations start ATG

<400> SEQUENCE: 4

| | |
|---|---|
| aagcttggat ccacatgatg atgcttctgg taatttatag tccaactagt cagtttattt | 60 |
| atttagaatc tttgtcctat cttttccgtca tttaccccctc ttttttttttt ttcttttcttt | 120 |
| ttagggtctc tttcgaaaat ttcatgccta tgctcggctc tcatacaacg tcactcatct | 180 |
| agaggcccaa caagtcccaa cctcccccctc caatattgaa atttgctttc accaagattt | 240 |
| gaacttcgat ctccaatgaa agagataaaa aatcatatca ttgaacttaa ggattcttgg | 300 |
| tgtccatcat ttgcatctta gcttcaatgc tttgattatt atactattta cggtttttttc | 360 |
| accagatccc tccaacaaat caataaattc accatatacc ctcaatgttt cagaaatgca | 420 |
| ccgtataccc ttgagtttcg aaaactatgc accagatccc cttttcctaa ctggcattaa | 480 |
| cccaccgtta gattatttac gatttttacca tcattaagcc ctaatcctaa tttaacctaa | 540 |

```
ccctaatcct acccctaaac ccttcccctt accctaaccc tacccccttgg cagccccac      600 accaccctc ccctccaccc caccccagcc cctaccctcc cctccccct ccccaccgc         660 tgatgtccgt gccagcctcc cccacccca ttgtcgctgc ttttgccggt ctcccccacc       720
ccatcgacgt tgcgcatgct ggcctcccca cctcctgcgc gtctgttcac cgctgacgac     780
tcctcacccc ttcccttcga acaccaaacc catacccctc cccttcgaac accggctaac    840
atcggctacc ttcgaatacc ccaccccatcc cccttcgaac accggctaat ttcgaacacc   900
aaacctcccc cacaccaccg gtctccccca cccctcccac acccttgaat ttcatcagtt    960
taaacttcta catattctag attttttaaa aattccttca agtttagaaa aacaataata    1020
gaacagagtt aattagtaaa attaagaaat ttttggttcc ttaatataaa atgtacaacc    1080
acgaagagac catccctatt ccgcatcaat atggaagagc catgtagccg ttaaaaatat    1140
ttgctttatt tgttgtttag agagcaaagt gtattatatt taaccctaaa ctttacggcc    1200
actaatggat attccctcta cgccgtatta ttttatacgt aattacgtat gcactgttat    1260
ataacctacc ttgaccatat ttgtctcgta acatataaag atatatgtta ggtataagat    1320
accaaggatc tttggtccag tagtatggct tcctatcttc gacatgggag accaaagttc    1380
gaatcttggt tgaagcaaaa tttcaatatt gttggagagg agggggggggg ggttgggctt   1440 gttgggcctc tgggtgagtg agtggccctg tgtgagggca gcccaaagaa aattcatctt    1500
accacgggtt ctcgaaagga gtccaaaaag acaatatata tattaggtat aagatattgt    1560
tggatttgtg gtaatgtata catatcaaaa tatcaacatt ctataacttt taataatcca    1620
ctagtattgc tgcggtgatt tgttgcgat tttacccata aacagcaata tatcacgtaa     1680
aaagaaaagg aaaaaatgta aaataagcag caatatggtt tcaagaaaat ttttttttgaa  1740 aaattttaac tgtttgacaa aacatattga tgcggtttct aagaaagaac cgcatcaata   1800
tattaaaata atatcaaaca atattctttg aacatattgt tgcaattcgt acaaaatatc   1860
gcagcaataa taggctttta aagggtccat ctagggtttt cttgttaagt tagtggatgg   1920
gtgtcgttta attctctcat ttactcggct agggtttcac tcctctcact ctctctcctc   1980
ctctcatcag ttttacgcct catcttctct cttttctctct ttgtatcatc agtttcacgc  2040
ctcatcttct cttaatcacg acgcaatgct ttaaccacca tgtactgcta actcgaaacc   2100
aggtcatcgc ttcaattgac tacaccgttt cttctccctc tcttttgtcc tcaccatgac   2160
gaagcaacac gctccatctt cgttcaacga gaaacgcgct aacatcccat agcgaagaaa   2220
atacctgaag atgaattcgg tctccgatga gtttggcggg ttatctttgt ttatcaattt    2280
tttttttttg tttttagat ctgtttctta attttttttcg ttatcatagc ggtggtctgt    2340
agtcatgatg tttgtatatc tcttttctttt tcttttttttt gggggtgaa ggcagtctgt   2400 ttttttttag gttagtgtta taggtagatc tattagtcaa attttgttat aaattctgta    2460
agaatatggt tctataaaat atatgagtgt aatgatgtaa gtttgtgttt tagttaagtg    2520
ttttatttga cactatctct tatcgtatat gaatatatat caaaaacaa atttctttt      2580 gagttgtagt acatatagct gcagttttttg gtaaaaaccg cagcaataag ctctaaatat   2640
ttttaataaa aaataaaacct attgctgcgg ttttggatag gaaccgcagc aatagctcgg   2700
cttattgctc tggtcagaaa ccatgacaat atgctaatta cctattgttg catccttaat    2760
tgctacgcgg ccaaaattgc agcaatatgc cacttaatga ccgcaacaat aaacaattat    2820
tctactagtg atcgataata aattatacta taggtcaaag ttgtgcatat tgacatgtgt    2880
taagtcaaac tgtatcgatt aatatgggaa gaaggaagta tgtaagaaaa tagcatcatg   2940
```

```
tgggatctta taatattcgt atcaatatgt atttgcaaaa tattaacttt tcacaaaatg   3000
ttttgaaagg atagagtcta ataatcaaag taataggtct attaaagtca taaatacccc   3060
taaaaaaatc ataaatacag ataatggagc aaaaattttg ggagagatta aaaattaaaa   3120
gtaattagga aagccatttc cataaggtta cttgtctttt cagagttgca cctattttta   3180
ctccactgca atggaataat actagaagca acatatataa tgtaattgga tattcttaca   3240
ttaatcaact aaataaaagg cctatatagt ctccaactag ttggacaatg agatgttaaa   3300
aaaaaaaaaa aaaaaaatta gttggacaat ggcatatgtt atatgttagc tatatgtcca   3360
ataaggcgac tgaaagacaa cctttaccaa attgataata ataaaaccat catcgtcaac   3420
cttcttatcc ttatgtgcct gaataatgag aacctagaca ttaccgaacg gctaacaaca   3480 agattttttac ccctaattaa gtcataacta gcgcattata tatcctttaa gtttgtcatt   3540
ctgtgatttc atttaatttt ctgtagtccc ttgccaagtc tgcctatata tatatagaag   3600
atggtgtatt gtaacttgtg acactaaatt ttcaagcatc ctcctagttt ccactttctc   3660
cttcatccac tcaacgcctt agctacgtaa gttaccaatt atgcattctc catcatacgc   3720
taatttacat tattgttaat gcttccttac atattgtttg atttaaacta ttttgtctta   3780
tcaaaattta tctgatctgg tcttattaga acttatctta tcttatatga atttaactta   3840
tattatctta tctgaactta tatcctagtt tattgtgtta tctaacatat atagttattc   3900
cgttttattc aacttattct atcgtatatc tgatataatc ttatcttatc ataacttgtt   3960
tttgttaaat aagtgaaaat aagttcaaca taacatataa tctcagtcat tcaatctgtt   4020
ttacactgtt ctttcacatt tagttgggaa tttttttaat ttttagcatt attattttcg   4080
tagacctgaa cttttcttta tctatatctc ttttttattcc cttttttgttg gtaatttaca   4140 aattctagaa taagactggt gcacaacaaa gtatcgtaag ttgggggaaa tttagcagtt   4200
atagaagtga ttacttacgg ttaaaactca cctatttttt tttctaaaag cgacttcttt   4260
tttacttaca aaattacccc tataaactta aaaagtgata ttttttagtct aaaagtaaaa   4320 gagtcttacc ataaattatt gtgtactcga tgctctcaag attttctatt gtttatatta   4380
ggaatatctt tgcagccctc tcgttagtaa agcttattcg aaattattac tattattcat   4440
gtccttgctt tagctaaaaa acgtcatctt ttcgttaaag ttgcaatttt cttaatccaa   4500
ttataattta catggttaac aatttcataa caaattactt actatttaac acttcctcca   4560 tttctttttaa ttacaatgct ttcacttttg catactattt attttacacc tcctccatct   4620
cttttagttg ctatacgctt tcacttttgc atactgttta tatataaatt ccaaaaagat   4680
ttattactaa cttatgcaaa taaatatcat tatgcaagat gtttagttct caatgtacac   4740
tggtgaacat ggacaaaaca ttagggaacc aagaattgaa cccccaatag attaaaaaat   4800
gaatatttac cattcattat ttattttttt gttctttgta gtccgttttt ctaaaaatta   4860 aaacaaaat atgcaaatcg caaaaaacat cttttcacttt tcagttgcca aatttcaaaa   4920
taaacatgat tagtttaagt ttaaaacctt agtttcatga tacagctatt atcatatgac   4980
tgtaaaagtc ttaattaaac cgaaaggttg gaatttatag cgtgatacccc aactgtccct   5040 ttacttctaa gagacgactt ttatatgtaa aagtatatgg gcccggacga tgctccgggt   5100
tttctctatg ctacaattta gtagtagtta ataagtcat ctcatttttca tttgaaaaag   5160 ttatcttatt cattatatag atttaaaag ttttccattc atatatcatt attaattttg   5220
attgaaaaaa caataatggt atggtggagt aatggttgga tctctttatt ttatacttga   5280
ggttgtgggt tcgaattttc acgtcaacaa ttctttattt ttactatatg agaaagacgt   5340
```

```
agataaaatg ttattgaatg agggatggtg acacgaggca catatacgtt cttaggaacg    5400
ccttttaata tattagtata gatttaaaac aacatacctt taatataagc caaaatataa    5460
ttggaggttt gagactttac ttgccccagc taaaattctc ctatgttgct gaacatcaaa    5520
atattttttt tgatccatat gagcctacaa agtacaaaga aggggagggg ggatttgaac    5580
ctgtgaccta tcgttcacat cacctcaatc ttaaccacta ggccaagaca tccttggtta    5640
ctgaacatca aaatataatt ggagggtaat tgttactatc taatagatta ttaaatatat    5700
taaagatcaa aaattataca ttcgaaagca tgaaagttaa acacgtaaca aacgaattaa    5760
gtatacgctg tattatttc atattttatg ctatgataca gatgcattag tgtgacaaga     5820
aaaccatgg                                                            5829

<210> SEQ ID NO 5
<211> LENGTH: 1117
<212> TYPE: DNA
<213> ORGANISM: Beta vulgaris
<220> FEATURE:
<221> NAME/KEY: misc_feature
<222> LOCATION: (1114)..(1116)
<223> OTHER INFORMATION: Translations start ATG

<400> SEQUENCE: 5
aagcttaaat gtgtaagcgg atttatgtta caagttattt gttagagata gatctaatta      60
tatgtactct tcttagattg attccatcaa atttcatcaa ccttagcatt tgccttcctg     120
tagcttgaag actggcgaca actgcttttg aagaaagaag aatgcggagt attgcttttg     180
cccacacaca tgctcctaca actccaaaat tgccagctct tatgcctatt ttgagaacca    240
tgttatcatg caaattgta tataatcaga tggtgtatgc acttttttgg acaagctcaa     300
ctaacagagc aacctaatgt aggaaggaaa caaatttaca agtattaaca tcttgccggc    360
attgctctaa ccaggaacat tagtcttata gtcttaaagt tattataggt taatgtgtat    420
tagatatcta cgtaaccgca tccaaattgc gcaaattcta caatatccgt aacacaacaa    480
acatacatct cactttgtt tcatagcgtg cgaaaccact ttactacttt gaggcaccta     540
aacgactaca aatagcacca ttctactatt tcggagaatc atacaatgcc tcaaaaacca    600
tgtagatgta atcaatttta gtacgcacac atatcctccg tgaattgacc actgcaattc    660
aaacaaatag tgtgcttacc acctatttga aatcaattac aaacaaatag caccgtactt    720
attataccta acgaattacg aataacaatt acgctatttt ggggtgccgc gcgcgtaaac    780
aactaatctc attcaaaaag gtcaaattag agacattgtg gttacgtact gcgcgccacc    840 taccccttc tcgggccttc atgacgtgtc ctatcacaat cttctgttga gataatcttt     900
ccaaccgcct aaccttttct tatcttaatt tttcttttcc ccttttaccg ccaaattaag    960
ccacaaaccc ttgtacacaa ctaaatgcac gcacatccgt ctgatcatct atcacccatg   1020
caatctcagc cgtttattat ttcttttttg tccctatat atataataat tcctccttta   1080
ataaatctta tcattcattc attgaataca tccatgg                            1117

<210> SEQ ID NO 6
<211> LENGTH: 28
<212> TYPE: DNA
<213> ORGANISM: Artificial Sequence
<220> FEATURE:
<223> OTHER INFORMATION: primer PHI5-1

<400> SEQUENCE: 6
gtgcaaggat tctggcaccc gtcggtgg                                          28
```

```
<210> SEQ ID NO 7
<211> LENGTH: 28
<212> TYPE: DNA
<213> ORGANISM: Artificial Sequence
<220> FEATURE:
<223> OTHER INFORMATION: primer PHI5-2

<400> SEQUENCE: 7
gtatgggccg cggcagatcc aggtagcg                                  28

<210> SEQ ID NO 8
<211> LENGTH: 25
<212> TYPE: DNA
<213> ORGANISM: Artificial Sequence
<220> FEATURE:
<223> OTHER INFORMATION: primer GAPDH-1

<400> SEQUENCE: 8
atgtttaagt acgacagtgt tcacg                                     25

<210> SEQ ID NO 9
<211> LENGTH: 25
<212> TYPE: DNA
<213> ORGANISM: Artificial Sequence
<220> FEATURE:
<223> OTHER INFORMATION: primer GAPDH-2

<400> SEQUENCE: 9
atgtgaaggt ctgacttgta ttcgt                                     25

<210> SEQ ID NO 10
<211> LENGTH: 18
<212> TYPE: DNA
<213> ORGANISM: Artificial Sequence
<220> FEATURE:
<223> OTHER INFORMATION: primer nptII gene

<400> SEQUENCE: 10
gtggagggct attcggta                                             18

<210> SEQ ID NO 11
<211> LENGTH: 20
<212> TYPE: DNA
<213> ORGANISM: Artificial Sequence
<220> FEATURE:
<223> OTHER INFORMATION: primer nptII gene

<400> SEQUENCE: 11
ccaccatgat attcggcaag                                           20
```